US008652125B2

(12) United States Patent
Keller (10) Patent No.: US 8,652,125 B2
(45) Date of Patent: Feb. 18, 2014

(54) ELECTROSURGICAL GENERATOR USER INTERFACE

(75) Inventor: Craig A. Keller, Boulder, CO (US)

(73) Assignee: Covidien LP, Mansfield, MA (US)

( * ) Notice: Subject to any disclaimer, the term of this patent is extended or adjusted under 35 U.S.C. 154(b) by 774 days.

(21) Appl. No.: 12/567,966

(22) Filed: Sep. 28, 2009

(65) Prior Publication Data

US 2011/0077631 A1    Mar. 31, 2011

(51) Int. Cl.
*A61B 18/14*    (2006.01)

(52) U.S. Cl.
USPC .................. 606/33; 606/34; 606/37; 606/38; 606/39; 606/40

(58) Field of Classification Search
USPC .................. 606/32–34, 37, 39–42, 45, 49–52
See application file for complete search history.

(56) References Cited

U.S. PATENT DOCUMENTS

| | | | |
|---|---|---|---|
| 3,699,967 A | 10/1972 | Anderson |
| 3,768,482 A | 10/1973 | Shaw |
| 3,826,263 A | 7/1974 | Cage et al. |
| 3,875,945 A | 4/1975 | Friedman |
| 3,913,583 A | 10/1975 | Bross |
| 3,923,063 A | 12/1975 | Andrews et al. |
| 3,952,748 A | 4/1976 | Kaliher et al. |
| 4,024,467 A | 5/1977 | Andrews et al. |
| 4,200,104 A | 4/1980 | Harris |
| 4,232,676 A | 11/1980 | Herczog |
| 4,314,559 A | 2/1982 | Allen |
| 4,429,694 A | 2/1984 | McGreevy |
| 4,438,766 A | 3/1984 | Bowers |
| 4,492,231 A | 1/1985 | Auth |
| 4,520,818 A | 6/1985 | Mickiewicz |
| 4,559,943 A | 12/1985 | Bowers |
| 4,727,874 A | 3/1988 | Bowers et al. |
| 4,739,759 A | 4/1988 | Rexroth et al. |
| 4,768,969 A | 9/1988 | Bauer et al. |
| 4,931,047 A | 6/1990 | Broadwin et al. |
| 5,015,227 A | 5/1991 | Broadwin et al. |
| 5,122,137 A | 6/1992 | Lennox |
| 5,190,517 A | 3/1993 | Zieve et al. |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

International Search Report EP10181018 dated Jan. 26, 2011.
U.S. Appl. No. 10/406,690, filed Apr. 3, 2003.
U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.

(Continued)

*Primary Examiner* — Michael Peffley
*Assistant Examiner* — Khadijeh Vahdat (57) ABSTRACT

An electrosurgical generator is disclosed. The generator includes an output stage configured to generate a waveform, a first input configured to adjust a cut setting representative of a cutting effect of the waveform, and a second input configured to adjust a hemostasis setting representative of a hemostasis effect of the waveform. The generator also includes a controller configured to receive cut and hemostasis settings and to adjust one of a duty cycle, a crest factor and a power level of the waveform to achieve a combined cutting and hemostasis effect based on the cut and hemostasis settings.

20 Claims, 4 Drawing Sheets

(56) References Cited

U.S. PATENT DOCUMENTS

| | | | |
|---|---|---|---|
| 5,290,283 A | 3/1994 | Suda | |
| 5,346,491 A | 9/1994 | Oertli | |
| 5,370,645 A | 12/1994 | Klicek et al. | |
| 5,403,311 A | 4/1995 | Abele et al. | |
| 5,403,312 A | 4/1995 | Yates et al. | |
| 5,409,485 A | 4/1995 | Suda | |
| 5,445,635 A | 8/1995 | Denen | |
| 5,472,443 A | 12/1995 | Cordis et al. | |
| 5,496,314 A | 3/1996 | Eggers | |
| 5,540,683 A | 7/1996 | Ichikawa | |
| 5,558,671 A | 9/1996 | Yates | |
| 5,588,432 A | 12/1996 | Crowley | |
| 5,626,575 A | 5/1997 | Crenner | |
| 5,693,042 A | 12/1997 | Bioarski et al. | |
| 5,707,369 A | 1/1998 | Vaitekunas et al. | |
| 5,720,744 A | 2/1998 | Eggleston et al. | |
| 5,817,093 A | 10/1998 | Williamson, IV et al. | |
| 5,830,212 A | 11/1998 | Cartmell | |
| 5,836,943 A | 11/1998 | Miller, III | |
| 5,843,019 A | 12/1998 | Eggers et al. | |
| 5,891,142 A | 4/1999 | Eggers et al. | |
| 5,931,836 A | 8/1999 | Hatta et al. | |
| 6,056,746 A | 5/2000 | Goble et al. | |
| 6,093,186 A | 7/2000 | Goble | |
| 6,123,701 A | 9/2000 | Nezhat | |
| 6,142,992 A | 11/2000 | Cheng et al. | |
| 6,228,078 B1 | 5/2001 | Eggers et al. | |
| 6,235,020 B1 | 5/2001 | Cheng et al. | |
| 6,238,387 B1 | 5/2001 | Miller, III | |
| 6,238,388 B1 | 5/2001 | Ellman | |
| 6,261,286 B1 | 7/2001 | Goble et al. | |
| 6,293,942 B1 | 9/2001 | Goble et al. | |
| 6,296,636 B1 | 10/2001 | Cheng et al. | |
| 6,306,134 B1 | 10/2001 | Goble et al. | |
| 6,364,877 B1 | 4/2002 | Goble et al. | |
| 6,383,183 B1 | 5/2002 | Sekino et al. | |
| 6,416,509 B1 | 7/2002 | Goble et al. | |
| 6,428,537 B1 | 8/2002 | Swanson et al. | |
| 6,458,122 B1 | 10/2002 | Pozzato | |
| 6,468,270 B1 | 10/2002 | Hovda et al. | |
| 6,482,201 B1 | 11/2002 | Olsen et al. | |
| 6,544,260 B1 | 4/2003 | Markel et al. | |
| 6,558,376 B2 | 5/2003 | Bishop | |
| 6,562,037 B2 | 5/2003 | Paton | |
| 6,626,901 B1 | 9/2003 | Treat et al. | |
| 6,632,193 B1 | 10/2003 | Davison et al. | |
| 6,733,498 B2 | 5/2004 | Paton | |
| 6,740,079 B1 | 5/2004 | Eggers | |
| 6,809,508 B2 | 10/2004 | Donofrio | |
| 6,837,888 B2 | 1/2005 | Ciarrocca et al. | |
| 6,890,331 B2 | 5/2005 | Kristensen | |
| 6,923,804 B2 | 8/2005 | Eggers et al. | |
| 6,974,453 B2 | 12/2005 | Woloszko et al. | |
| 6,977,495 B2 | 12/2005 | Donofrio | |
| 7,004,174 B2 | 2/2006 | Eggers et al. | |
| 7,008,421 B2 | 3/2006 | Daniel et al. | |
| 7,025,764 B2 | 4/2006 | Paton et al. | |
| 7,083,618 B2 | 8/2006 | Couture et al. | |
| 7,094,231 B1 | 8/2006 | Ellman et al. | |
| 7,147,638 B2 | 12/2006 | Chapman et al. | |
| 7,156,844 B2 | 1/2007 | Reschke et al. | |
| 7,156,846 B2 | 1/2007 | Dycus et al. | |
| 7,223,264 B2 | 5/2007 | Daniel et al. | |
| 7,341,586 B2 | 3/2008 | Daniel et al. | |
| 7,470,272 B2 | 12/2008 | Mulier et al. | |
| 7,491,201 B2 | 2/2009 | Shields et al. | |
| 7,513,896 B2 | 4/2009 | Orszulak | |
| 2003/0181898 A1 | 9/2003 | Bowers | |
| 2004/0030330 A1 | 2/2004 | Brassell et al. | |
| 2004/0068304 A1 | 4/2004 | Paton et al. | |
| 2004/0097913 A1 | 5/2004 | Refior | |
| 2004/0143263 A1 | 7/2004 | Schechter et al. | |
| 2004/0260279 A1* | 12/2004 | Goble et al. | 606/34 |
| 2005/0004634 A1 | 1/2005 | Ricart et al. | |
| 2005/0113824 A1* | 5/2005 | Sartor et al. | 606/42 |
| 2005/0182398 A1 | 8/2005 | Paterson | |
| 2005/0203504 A1 | 9/2005 | Wham et al. | |
| 2006/0025760 A1 | 2/2006 | Podhajsky | |
| 2007/0173803 A1* | 7/2007 | Wham et al. | 606/34 |
| 2007/0173804 A1 | 7/2007 | Wham et al. | |
| 2007/0173806 A1 | 7/2007 | Orszulak et al. | |
| 2007/0173809 A1* | 7/2007 | Goble | 606/37 |
| 2007/0173813 A1 | 7/2007 | Odom | |
| 2008/0039831 A1 | 2/2008 | Odom et al. | |
| 2008/0039836 A1 | 2/2008 | Odom et al. | |
| 2008/0119843 A1 | 5/2008 | Morris | |
| 2008/0294156 A1* | 11/2008 | Newton et al. | 606/34 |
| 2009/0069801 A1* | 3/2009 | Jensen et al. | 606/34 |
| 2009/0157071 A1 | 6/2009 | Wham et al. | |
| 2009/0157072 A1 | 6/2009 | Wham et al. | |
| 2009/0157073 A1 | 6/2009 | Orszulak | |
| 2009/0157075 A1 | 6/2009 | Wham et al. | |
| 2009/0240244 A1 | 9/2009 | Malis | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 878169 | 11/1998 |
| EP | 1051948 | 11/2000 |
| EP | 1151725 | 11/2001 |
| EP | 1301135 | 4/2003 |
| EP | 1535581 | 6/2005 |
| EP | 1609430 | 12/2005 |
| EP | 880220 | 6/2006 |
| EP | 1707143 | 10/2006 |
| EP | 1810628 | 7/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO96/02180 | 2/1996 |
| WO | WO96/39914 | 12/1996 |
| WO | WO98/07378 | 2/1998 |
| WO | WO02/11634 | 2/2002 |
| WO | WO02/45589 | 6/2002 |
| WO | WO03/090635 | 11/2003 |
| WO | WO03/092520 | 11/2003 |
| WO | WO2004/103156 | 12/2004 |

(56) References Cited

FOREIGN PATENT DOCUMENTS

| WO | WO2005/060849 | 7/2005 |
|---|---|---|
| WO | WO 2005117735 | 12/2005 |
| WO | WO2006/050888 | 5/2006 |

OTHER PUBLICATIONS

U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.
U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.

Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23,.2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.

* cited by examiner

ELECTROSURGICAL GENERATOR USER INTERFACE

BACKGROUND

1. Technical Field

The present disclosure relates to electrosurgical apparatuses, systems and methods. More particularly, the present disclosure is directed to an electrosurgical generator having a user interface for selecting desired electrosurgical effects on tissue.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current, microwave energy or resistive heating to a surgical site to cut, ablate, coagulate or seal tissue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

SUMMARY

According to one embodiment of the present disclosure, an electrosurgical generator is disclosed. The generator includes an output stage configured to generate a waveform, a first input configured to adjust a cut setting representative of a cutting effect of the waveform, and a second input configured to adjust a hemostasis setting representative of a hemostasis effect of the waveform. The generator also includes a controller configured to receive cut and hemostasis settings and to adjust one or more characteristics of the waveform to achieve a combined cutting and hemostasis effect based on the cut and hemostasis settings. The waveform characteristics adjusted may include one of a duty cycle, a crest factor, a frequency, a pulse width, a pulse sequence, and a power level, or combination thereof.

A method for controlling an electrosurgical generator is also contemplated by the present disclosure. The method includes the steps of: adjusting a cut setting representative of a cutting effect of a waveform and adjusting a hemostasis setting representative of a hemostasis effect of the waveform. The method also includes the step of adjusting a waveform parameter of the waveform to achieve a combined cutting and hemostasis effect based on the cut and hemostasis settings.

According to another embodiment of the present disclosure, an electrosurgical system is disclosed. The system includes an electrosurgical generator having an output stage configured to generate a waveform suitable to impart cutting and hemostasis effects on tissue. The generator also includes a first input configured to adjust a cut setting representative of the cutting effect of the waveform and a second input configured to adjust a hemostasis setting representative of the hemostasis effect of the waveform. The generator further includes a controller configured to receive cut and hemostasis settings and to adjust a parameter of the waveform to achieve a combined cutting and hemostasis effect based on the cut and hemostasis settings. The system also includes an electrosurgical instrument configured to couple to the electrosurgical generator and to supply the waveform to the tissue.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and/or bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1:
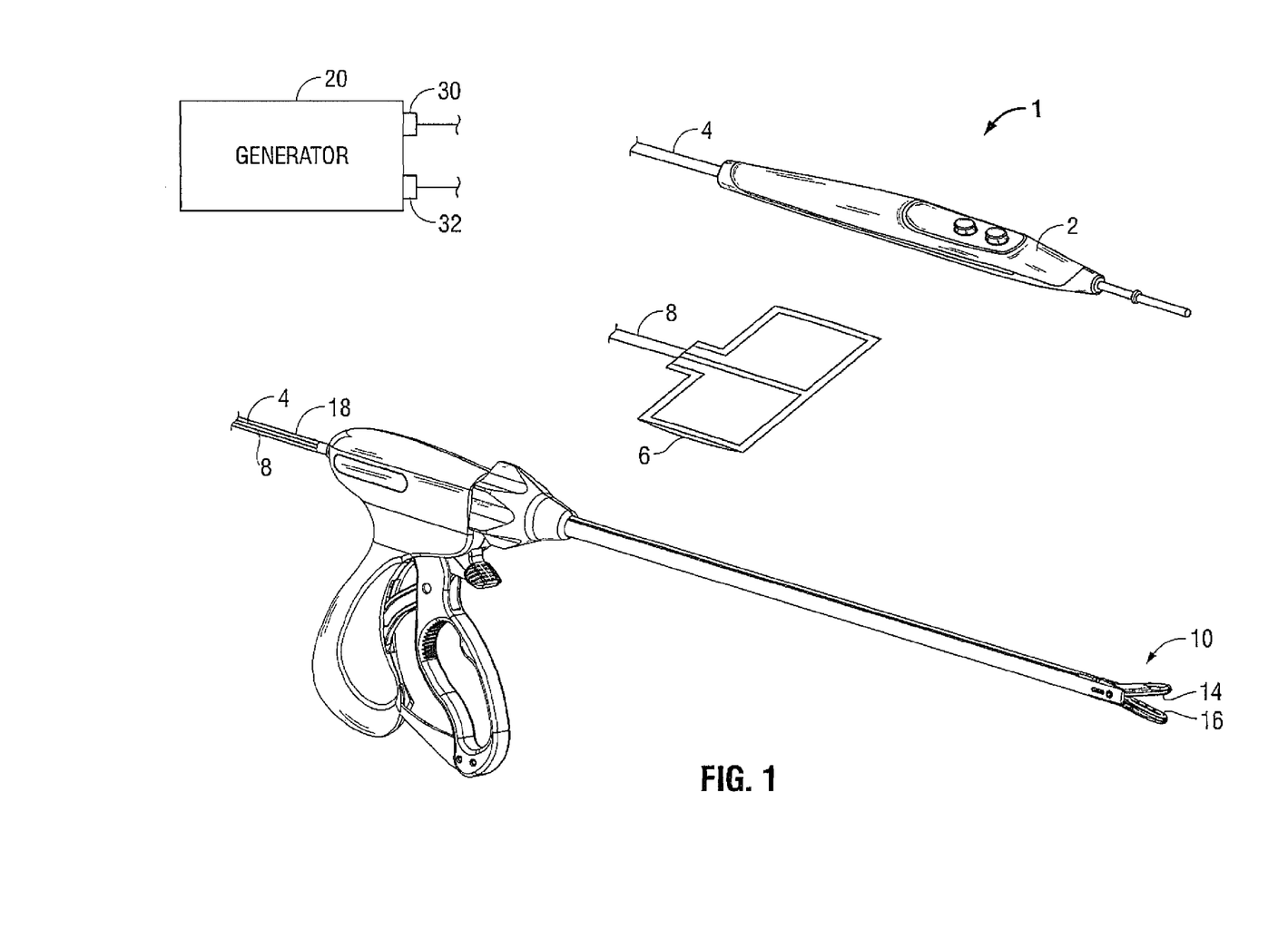
FIG. 1 is a schematic block diagram of an electrosurgical system according to one embodiment of the present disclosure.

FIG. 1 is a schematic illustration of a bipolar and monopolar electrosurgical system 1 according to one embodiment of the present disclosure. The system 1 includes one or more monopolar electrosurgical instruments 2 having one or more electrodes (e.g., electrosurgical cutting probe, ablation electrode(s), etc.) for treating tissue of a patient. Electrosurgical energy is supplied to the instrument 2 by a generator 20 via a supply line 4 that is connected to an active terminal 30 (FIG. 3) of the generator 20, allowing the instrument 2 to coagulate, ablate and/or otherwise treat tissue. The energy is returned to the generator 20 through a return electrode 6 via a return line 8 at a return terminal 32 (FIG. 3) of the generator 20. The system 1 may include a plurality of return electrodes 6 that are arranged to minimize the chances of tissue damage by maximizing the overall contact area with the patient. In addition, the generator 20 and the return electrode 6 may be configured for monitoring so-called "tissue-to-patient" contact to insure that sufficient contact exists therebetween to further minimize chances of tissue damage.

The system 1 may also include a bipolar electrosurgical forceps 10 having one or more electrodes for treating tissue of a patient. The electrosurgical forceps 10 includes opposing jaw members having one or more active electrodes 14 and a return electrode 16 disposed therein. The active electrode 14 and the return electrode 16 are connected to the generator 20 through cable 18 that includes the supply and return lines 4, 8 coupled to the active and return terminals 30, 32, respectively. The electrosurgical forceps 10 is coupled to the generator 20 at a connector having connections to the active and return terminals 30 and 32 (e.g., pins) via a plug disposed at the end of the cable 18, wherein the plug includes contacts from the supply and return lines 4, 8.

Figure 2:
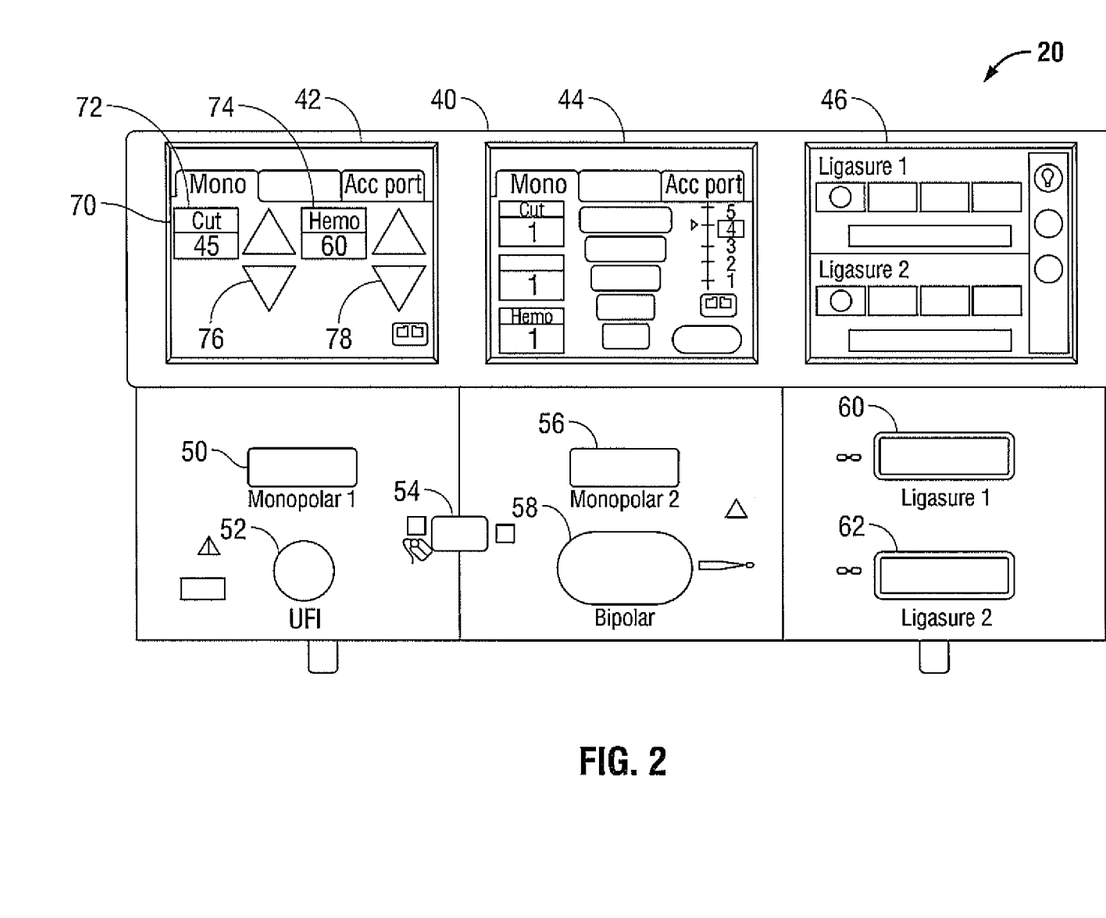
FIG. 2 is a front view of an electrosurgical generator according to an embodiment of the present disclosure.

The generator 20 may be any suitable type (e.g., electrosurgical, microwave, etc.) and may include a plurality of connectors 50-62 to accommodate various types of electrosurgical instruments (e.g., multiple instruments 2, electrosurgical forceps 10, etc.). With reference to FIG. 2, front face 40 of the generator 20 is shown. The generator 20 includes one or more display screens 42, 44, 46 for providing the user with variety of output information (e.g., intensity settings, treatment complete indicators, etc.). Each of the screens 42, 44, 46 is associated with a corresponding connector 50-62. The generator 20 includes suitable input controls (e.g., buttons, activators, switches, touch screen, etc.) for controlling the generator 20. The display screens 42, 44, 46 are also configured as touch screens that display a corresponding menu for the electrosurgical instruments (e.g., multiple instruments 2, electrosurgical forceps 10, etc.). The user then makes inputs by simply touching corresponding menu options.

The screen 46 controls bipolar sealing procedures performed by the forceps 10 that may be plugged into the connectors 60 and 62. The generator 20 outputs energy through the connectors 60 and 62 suitable for sealing tissue grasped by the forceps 10. The screen 42 controls monopolar output and the devices connected to the connectors 50 and 52. The connector 50 is configured to couple to the instrument 2 and the connector 52 is configured to couple to a foot switch (not shown). The foot switch provides for additional inputs (e.g., replicating inputs of the generator 20 and/or instrument 2). The screen 44 controls monopolar and bipolar output and the devices connected to the connectors 56 and 58. Connector 56 is configured to couple to the instrument 2, allowing the generator 20 to power multiple instruments 2. Connector 58 is configured to couple to a bipolar instrument (not shown). When using the generator 20 in monopolar mode (e.g., with instruments 2), the return electrode 6 is coupled to the connector 54, which is associated with the screens 42 and 44. The generator 20 is configured to output the modes discussed above through the connectors 50, 56, 58.

Figure 3:
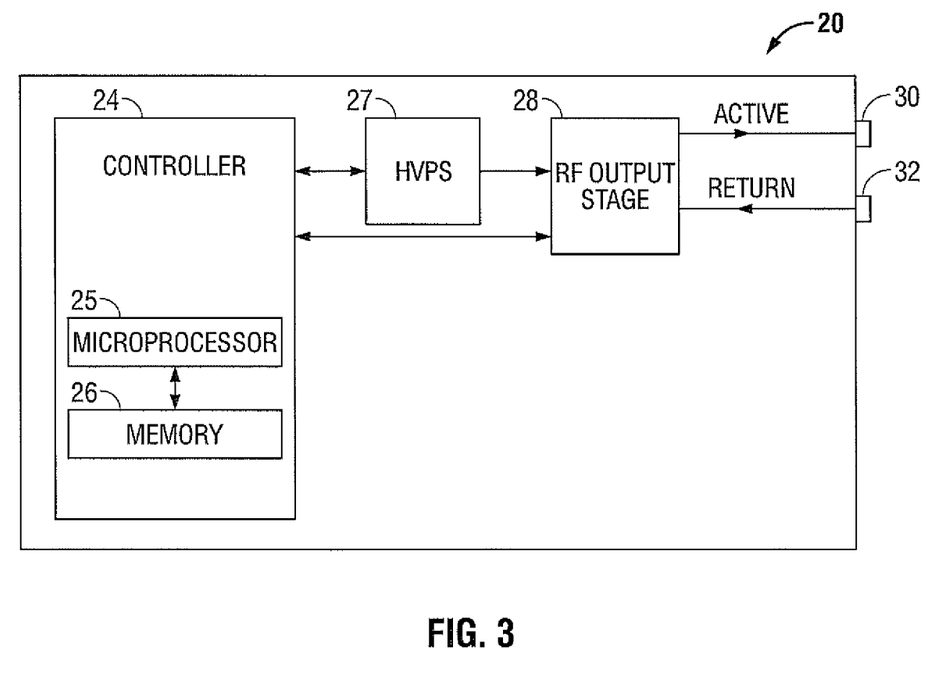
FIG. 3 is a schematic block diagram of the electrosurgical generator of FIG. 2 according to an embodiment of the present disclosure.

FIG. 3 shows a schematic block diagram of the generator 20 configured to output electrosurgical energy. In another embodiment, the generator 20 may be configured to output other types of energy such as, microwave, laser, etc. to power various other tissue treatment devices, such as microwave antennas, ultrasonic forceps, lasers, resistive heating electrodes, etc. The generator 20 includes a controller 24, a high voltage DC power supply 27 ("HVPS") and an output stage 28. The HVPS 27 is connected to an AC source (e.g., electrical wall outlet) and provides high voltage DC power to an output stage 28, which then converts high voltage DC power into treatment energy (e.g., laser, ultrasonic, electrosurgical or microwave) and delivers the energy to the active terminal 30. The energy is returned thereto via the return terminal 32. The output stage 28 is configured to operate in a plurality of modes, during which the generator 20 outputs corresponding waveforms having specific duty cycles, peak voltages, crest factors, etc. In another embodiment, the generator 20 may be based on other types of suitable power supply topologies.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop, in which a plurality of sensors measure a variety of tissue and energy properties (e.g., tissue impedance, tissue temperature, output power, current and/or voltage, etc.), and provide feedback to the controller 24. Such sensors are within the purview of those skilled in the art. The controller 24 then signals the HVPS 27 and/or output stage 28, which then adjusts the DC and/or power supply, respectively. The controller 24 also receives input signals from the input controls of the generator 20, the instrument 2 or forceps 10. The controller 24 utilizes the input signals to adjust power outputted by the generator 20 and/or performs other control functions thereon.

The generator 20 is configured to operate under a variety of electrosurgical modes and output a variety of corresponding waveforms that impart a suitable amount of hemostasis and cutting effect on the tissue. The cutting effect controls the rate at which the tissue is vaporized, whereas the hemostasis effect corresponds to the thickness of the remaining tissue affected. Conventional generators provide only for selection of a limited number of electrosurgical modes that impart a predetermined ratio of cut to hemostasis effects. In particular, selection of the cut mode provides for a continuous waveform that provides mostly cutting with very little hemostasis. The fulgurate mode, in contrast, utilizes a waveform that produces hemostasis with very little cutting action. The user usually controls the power output for each of the modes based on the power curve. In other words, the power curve is shifted based on the increase or decrease in power as set by the user. These controls are more closely tied to the internal operation of the generator 20 than to the effects on the tissue, which are of specific interest to the user. These selections provide access to a discrete set of waveforms with effects ranging from traditional pure cut to the fulgurate and spray modes discussed above.

With reference to FIG. 2, the present disclosure provides an improved user-interface 70 that allows the user to select a desired tissue effect based on a categorization of the cut and hemostasis effects imparted on the tissue as opposed to selecting specific electrosurgical modes. In other words, the user-interface 70 provides for a natural separation for the user of the two primary electrosurgical effects, namely, cutting and hemostasis. The user-interface 70 allows the user to control amount of cut and amount of hemostasis that is to be produced by the waveform. The two selections are independent of each other and are mapped by the generator 20 to the specific operating parameters needed to provide the selected effect.

The user-interface 70 includes a cut setting indicator 72 and a hemostasis setting indicator 74. The settings 72 and 74 are controlled by corresponding inputs 76 and 78, which are shown as a pair of up and down arrows. The user may adjust the amount of cutting and hemostasis effect through the inputs 76 and 78 to achieve a desired tissue effect. The inputs 76 and 78 may be configured using various input controls (e.g., buttons, activators, switches, touch screen, etc.). The user can adjust the amount of hemostasis and cutting effects without adversely affecting the competing tissue effects. The cut and hemostasis settings are then interpreted by the generator 20 to output a corresponding waveform.

The settings 72 and 74 may be represented on a scale as shown in FIG. 2. In one embodiment, the scale may be from 0 to 100 with adjustments to be made in increments of 5 or 10. In another embodiment, the scale may be configured to represent the rate of the cutting effect (e.g. in millimeters$^2$ or millimeters$^3$ per second) and the thickness of the hemostasis effect (e.g., in millimeters or inches).

Figure 4:
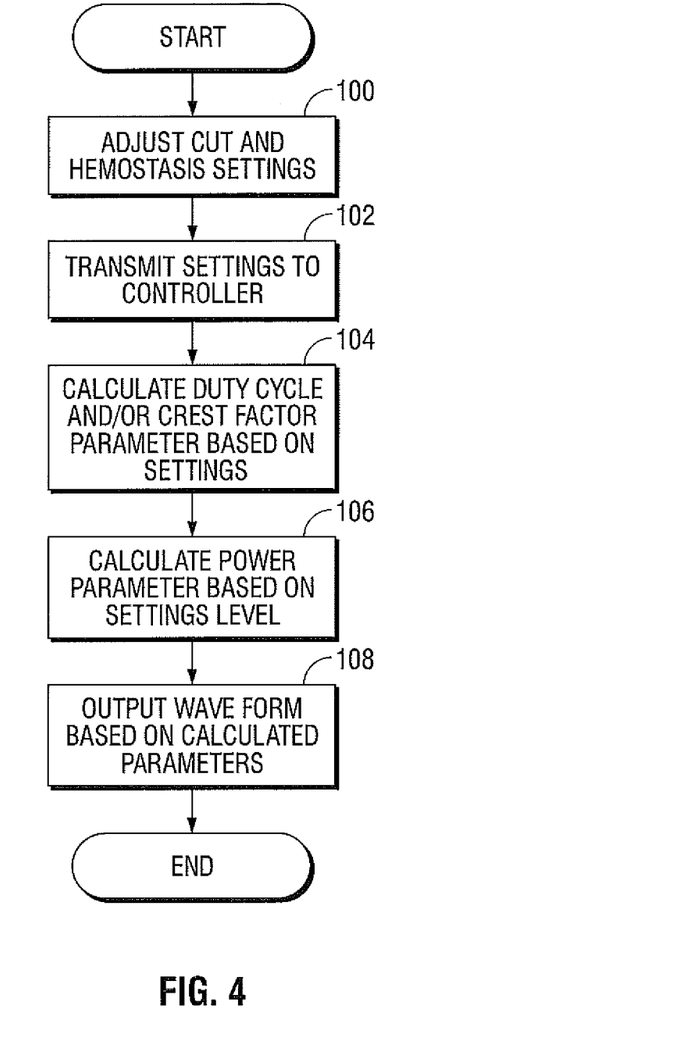
FIG. 4 is a flow chart of a method according to an embodiment of the present disclosure.

FIG. 4 shows a method according to one embodiment of the present disclosure for outputting a specific waveform based on the cut and hemostasis settings 72 and 74. In step 100, the user selects the settings 72 and 74 through the inputs 76 and 78. In step 102, the settings 72 and 74 are interpreted by the controller 24 to generate a suitable electrosurgical waveform. In step 104, the controller 24 selects a duty cycle and/or crest factor parameter for the waveform based on the combination of the settings 72 and 74. More specifically, a higher duty cycle imparts a larger cutting effect on tissue, whereas a lower duty cycle (e.g., pulsatile) waveforms result in a larger hemostasis effect. In step 106, the controller 24 selects a power setting parameter based on the combination of the settings 72 and 74. Higher power is used to impart greater cutting and/or hemostasis effects. In step 108, the controller 24 signals the output stage 28 to output the waveform based on the parameters (e.g., duty cycle, crest factor, power settings) as calculated in the previous steps 104-106.

The settings 72 and 74 may be adjusted in real time during the procedure. The user-interface 70 is specifically useful for quickly modifying the output of the generator 20 without switching between various output modes. During cutting procedures, upon encountering excessive bleeding at the tissue, the user may increase the hemostasis effect without decreasing the cutting effect. Conversely, during hemostasis procedures, upon encountering difficulty in cutting, the user can increase the cutting effect without modifying the hemostasis effect (e.g., the amount of tissue affected along the margins of the cut).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
    an output stage configured to generate a waveform suitable to simultaneously impart a cutting effect and hemostasis effect on tissue;
    a first input configured to adjust a cut setting representative of the cutting effect of the waveform in real time during the simultaneous imparting of the cutting and hemostasis effects on the tissue without changing the hemostasis effect;
    a second input configured to adjust a hemostasis setting representative of the hemostasis effect of the waveform in real time during the simultaneous imparting of the cutting and hemostasis effects on the tissue without changing the cutting effect; and
    a controller configured to receive the cut and hemostasis settings in real time and adjust at least one of a duty cycle, a crest factor and a power level of the waveform to achieve the simultaneous cutting and hemostasis effects based on the cut and hemostasis settings, the cut and hemostasis settings being adjustable to independently adjust each of the cutting and hemostasis effects imparted by the waveform.

2. The electrosurgical generator according to claim 1, wherein the waveform is selected from a group consisting of an RF electrosurgical waveform and a microwave waveform.

3. The electrosurgical generator according to claim 1, further comprising:
    at least one display screen configured to output the cut setting and the hemostasis setting.

4. The electrosurgical generator according to claim 3, wherein the at least one display screen is a touch screen.

5. The electrosurgical generator according to claim 4, wherein the at least one display screen is configured to output a user interface including the first and second inputs.

6. The electrosurgical generator according to claim 3, wherein each of the cut and hemostasis settings displays a scale representative of the cutting effect and the hemostasis effect of the waveform, respectively.

7. The electrosurgical generator according to claim 6, wherein the displayed scale of the cut setting represents a rate of the cutting effect and the displayed scale of the hemostasis setting represents a thickness of the hemostasis effect.

8. A method for controlling an electrosurgical generator, the method comprising the steps of:
    outputting a waveform suitable to simultaneously impart a cutting effect and hemostasis effect on tissue;
    adjusting a cut setting representative of the cutting effect of the waveform in real time during the simultaneous imparting of the cutting and hemostasis effects on the tissue without changing the hemostasis effect;
    adjusting a hemostasis setting representative of the hemostasis effect of the waveform in real time during the simultaneous imparting of the cutting and hemostasis effects on the tissue without changing the cutting effect; and
    adjusting at least one waveform parameter of the waveform to achieve the simultaneous cutting and hemostasis effects based on the cut and hemostasis settings, the cut and hemostasis settings being adjustable to independently adjust each of the cutting and hemostasis effects of the waveform.

9. The method according to claim 8, wherein the at least one waveform parameter is selected from a group consisting of a duty cycle, a crest factor and a power level.

10. The method according to claim 8, further comprising the step of:
    displaying the cut setting and the hemostasis setting on at least one display screen including a touch screen.

11. The method according to claim 10, further comprising the step of:

outputting a user interface including a first input configured to adjust the cut setting and a second input configured to adjust the hemostasis setting on the at least one display screen.

12. The method according to claim 10, wherein the displaying step further includes the step of displaying each of the cut and hemostasis settings as a scale representative of the cutting effect and the hemostasis effect of the waveform, respectively.

13. An electrosurgical system, comprising:
an electrosurgical generator, comprising:
an output stage configured to generate a waveform suitable to simultaneously impart a cutting effect and a hemostasis effect on tissue;
a first input configured to adjust a cut setting representative of the cutting effect of the waveform in real time during the simultaneous imparting of the cutting and hemostasis effects on the tissue without changing the hemostasis effect;
a second input configured to adjust a hemostasis setting representative of the hemostasis effect of the waveform in real time during the simultaneous imparting of the cutting and hemostasis effects on the tissue without changing the cutting effect; and
a controller configured to receive the cut and hemostasis settings in real time and adjust at least one parameter of the waveform to achieve the simultaneous cutting and hemostasis effects based on the cut and hemostasis settings, the cut and hemostasis settings being adjustable to independently adjust each of the cutting and hemostasis effects imparted by the waveform; and
at least one electrosurgical instrument configured to couple to the electrosurgical generator and to supply the waveform to the tissue.

14. The electrosurgical system according to claim 13, wherein the at least one parameter is selected from a group consisting of a duty cycle, a crest factor and a power level.

15. The electrosurgical system according to claim 13, further comprising:
at least one display screen configured to output the cut setting and the hemostasis setting.

16. The electrosurgical system according to claim 15, wherein the at least one display screen is a touch screen.

17. The electrosurgical system according to claim 16, wherein the at least one display screen is configured to output a user interface including the first and second inputs.

18. The electrosurgical system according to claim 15, wherein each of the cut and hemostasis settings displays a scale representative of the cutting effect and the hemostasis effect of the waveform, respectively.

19. The electrosurgical generator according to claim 18, wherein the displayed scale of the cut setting represents a rate of the cutting effect and the displayed scale of the hemostasis setting represents a thickness of the hemostasis effect.

20. The electrosurgical generator according to claim 13, wherein the waveform is selected from a group consisting of an RF electrosurgical waveform and a microwave waveform.

* * * * *